(12) United States Patent
Burbar et al.

(10) Patent No.: US 11,793,474 B2
(45) Date of Patent: *Oct. 24, 2023

(54) LIGHTING ARRANGEMENT FOR A MEDICAL IMAGING SYSTEM

(71) Applicant: Siemens Medical Solutions USA, Inc., Malvern, PA (US)

(72) Inventors: Ziad Burbar, Knoxville, TN (US); James L. Corbeil, Knoxville, TN (US); Jeffrey Bostrom, Clinton, TN (US); James Williams, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/188,513

(22) Filed: Mar. 23, 2023

(65) Prior Publication Data
US 2023/0218246 A1   Jul. 13, 2023

Related U.S. Application Data

(63) Continuation of application No. 16/949,229, filed on Oct. 21, 2020, now Pat. No. 11,647,971.

(51) Int. Cl.
*A61B 6/08* (2006.01)
*A61B 6/03* (2006.01)
*A61B 90/00* (2016.01)

(52) U.S. Cl.
CPC .............. *A61B 6/08* (2013.01); *A61B 6/032* (2013.01); *A61B 6/037* (2013.01); *A61B 90/36* (2016.02);

(Continued)

(58) Field of Classification Search
CPC .......... A61B 6/032; A61B 90/36; A61B 6/08; A61B 6/037; A61B 2090/3618;
(Continued)

(56) References Cited

U.S. PATENT DOCUMENTS 5,469,488 A    11/1995  Ono
11,647,971 B2 *  5/2023  Burbar ..................... A61B 6/08
                                                                   378/206
(Continued)

FOREIGN PATENT DOCUMENTS

WO       2019165302        8/2019

*Primary Examiner* — Irakli Kiknadze

(57) ABSTRACT

A lighting arrangement for a medical imaging system having a cylindrical wall that forms a tunnel that receives a patient to be scanned. The lighting arrangement includes a transparent wall section formed in the wall, wherein the transparent wall section extends along a transparent portion of a wall circumference. The imaging system also includes a lighting device located adjacent an outer surface of the transparent wall section. The lighting device extends along a device portion of a wall circumference corresponding to the transparent portion wherein light emitted by the lighting device is transmitted through the transparent wall section in a direction orthogonal to a longitudinal axis of the tunnel to circumferentially illuminate the tunnel. In addition, a system status is indicated by a color of light emitted by the LEDs. Further, light emitted by the lighting device varies in intensity to indicate a changing count rate.

21 Claims, 5 Drawing Sheets

(52) U.S. Cl.
CPC .............. *A61B 2090/3614* (2016.02); *A61B 2090/3618* (2016.02)

(58) Field of Classification Search
CPC ...... A61B 2090/309; A61B 2090/3614; A61B 6/04; A61B 6/4417; A61B 6/461; A61B 5/0555; A61B 5/486; A61B 6/0407; A61B 6/4441; A61B 6/467; A61B 5/055; A61B 6/102; A61B 6/5294; A61B 6/464; A61B 6/0492; A61B 6/105; A61B 6/12; A61B 6/4225; A61B 6/547; A61B 90/08; A61B 90/13; A61B 90/25; A61B 90/37; A61B 90/39; A61B 90/50; A61B 2017/0092; A61B 2090/3764; A61B 2090/3937; A61B 2090/3983; A61B 90/11; A61B 5/0033; A61B 5/742; A61B 17/2256; A61B 17/1703; A61B 17/1721; A61B 34/20; A61B 5/064; A61B 6/4405; A61M 21/02; A61M 21/00; G01R 33/28; G01R 33/288
USPC ......................................................... 378/206
See application file for complete search history.

(56) References Cited

U.S. PATENT DOCUMENTS

| | | |
|---|---|---|
| 2002/0065461 A1 | 5/2002 | Cosman |
| 2003/0036692 A1 | 2/2003 | Landi et al. |
| 2005/0004444 A1 | 1/2005 | Boninger et al. |
| 2009/0154647 A1 | 6/2009 | Matsuzawa et al. |
| 2010/0056902 A1 | 3/2010 | Granzer et al. |
| 2013/0345543 A1 | 12/2013 | Steilbel et al. |
| 2019/0143145 A1 | 5/2019 | Laurence et al. |
| 2021/0345976 A1 | 11/2021 | Brown et al. |

\* cited by examiner

LIGHTING ARRANGEMENT FOR A MEDICAL IMAGING SYSTEM

CROSS REFERENCE TO RELATED APPLICATION

This application is a continuation application of copending application Ser. No. 16/949,229, filed Oct. 21, 2020 and entitled LIGHTING ARRANGEMENT FOR A MEDICAL IMAGING SYSTEM which is hereby incorporated by reference herein in its entirety.

TECHNICAL FIELD

Aspects of the present invention relate to a lighting arrangement for illuminating a patient tunnel of a medical imaging system, and more particularly, to a lighting arrangement that includes a transparent wall section formed in a wall of the imaging system and a lighting device located adjacent an outer surface of the transparent wall section wherein light emitted by the lighting device is transmitted through the transparent wall section in a direction orthogonal to a longitudinal axis of the tunnel to circumferentially illuminate the tunnel.

BACKGROUND

Medical imaging systems include a patient bore that receives a patient to be imaged or scanned. The bore is typically elongated and forms a cylindrically shaped patient tunnel through which the patient is moved in a longitudinal direction along a longitudinal axis of the tunnel. The tunnel may be imposing or intimidating to those that are either young or for adults who suffer from claustrophobia, for example. This effect is becoming more pronounced as the average bore length of medical imaging systems, such as positron-emission tomography/computed tomography (PET/CT) systems, is trending longer. In particular, imaging systems having extended axial field-of-views (FoVs), coupled with bore diameters that have remained largely unchanged, have made PET systems less appealing since patients frequently experience a "closed-space feeling" or claustrophobia when located in the tunnel. This is especially true in imaging systems having even longer tunnels such as MR-PET imaging systems and imaging systems having FoVs that are a meter long or more.

The addition of light in the tunnel ameliorates the look and feel of the system and gives the tunnel an appearance of being spacious, thus lessening the effects of claustrophobia. For example, lights may be incorporated into the front and back covers of the tunnel. In addition, light projectors located on the longitudinal axis of the tunnel may be used to direct light in a longitudinal direction through the tunnel.

SUMMARY OF THE INVENTION

A lighting arrangement for a medical imaging system is disclosed wherein the imaging system includes a cylindrical wall that forms a tunnel that receives a patient to be scanned. The lighting arrangement includes a transparent wall section formed in the wall, wherein the transparent wall section extends along a transparent portion of a wall circumference. The imaging system also includes a lighting device located adjacent an outer surface of the transparent wall section. The lighting device extends along a device portion of a wall circumference corresponding to the transparent portion wherein light emitted by the lighting device is transmitted through the transparent wall section in a direction substantially orthogonal to a longitudinal axis of the tunnel to circumferentially illuminate the tunnel. In addition, a system status is indicated by a color of light emitted by the LEDs. Further, light emitted by the lighting device varies in intensity to indicate a changing count rate.

In addition, a method of illuminating a tunnel of a medical imaging system is disclosed wherein the imaging system includes a cylindrical wall that forms the tunnel wherein the tunnel receives a patient to be scanned. The method includes providing a transparent wall section in the wall, wherein the transparent wall section extends along a transparent portion of a wall circumference. The method also includes locating a lighting device adjacent an outer surface of the transparent wall section, wherein the lighting device extends along a device portion of a wall circumference corresponding to the transparent portion. Further, the method includes transmitting light emitted by the lighting device through the transparent wall section in a direction substantially orthogonal to a longitudinal axis of the tunnel and circumferentially illuminating the tunnel. In addition, the method includes transmitting a color of light that is indicative of a system status.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which.

DETAILED DESCRIPTION

Figure 1:
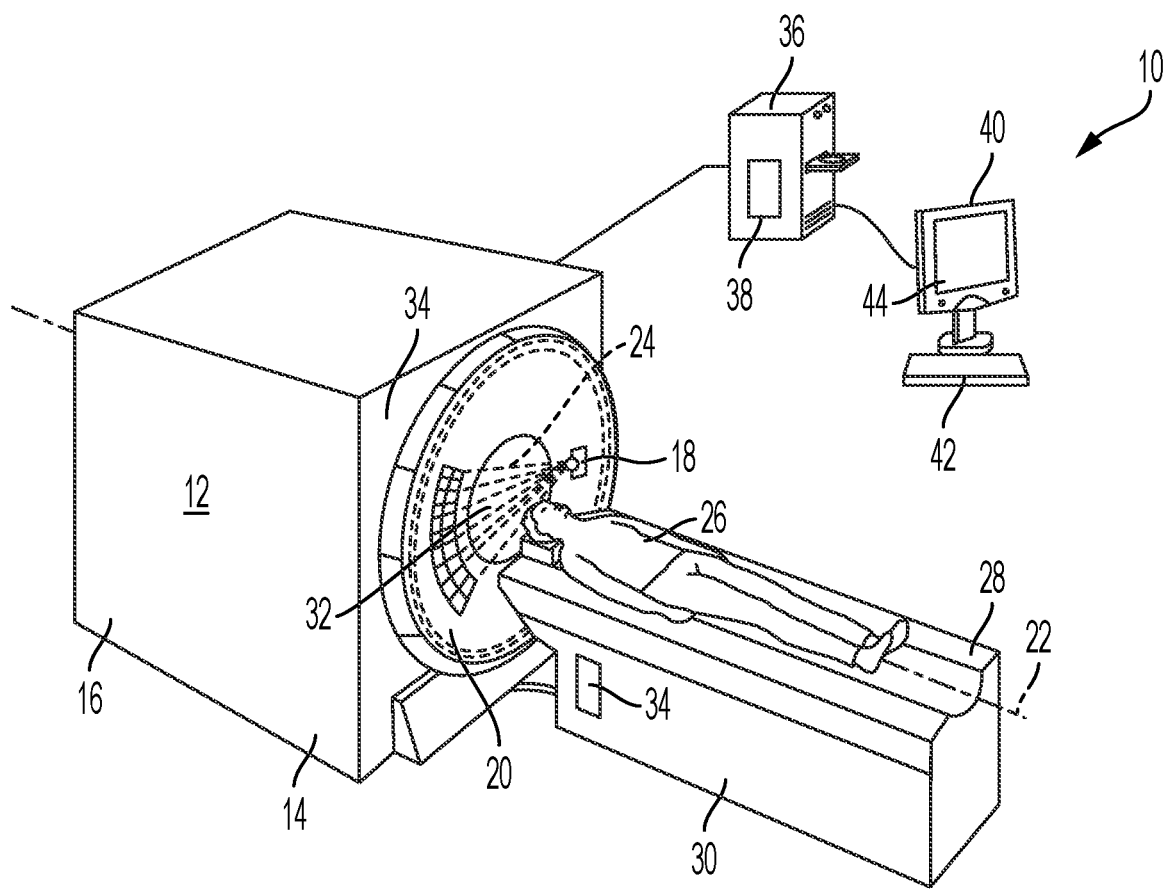
FIG. 1 depicts a medical imaging system in accordance with an aspect of the invention.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Referring to FIG. 1, a view of an exemplary medical imaging system 10 in accordance with an aspect of the invention is shown. The invention may be used in conjunction with any medical imaging system 10 having a patient tunnel for receiving a patient such as a magnetic resonance imaging (MRI) system, a positron emission tomography (PET) system, a single-photon emission computed tomography (SPECT) system, a PET/MRI system, an X-ray computed tomography (CT) system, a PET/CT system, a SPECT/CT system and others. For purposes of illustration, the invention will be described in connection with a PET/CT imaging system 12 having a CT portion 14 and a PET portion 16. The CT portion 14 includes a recording unit, comprising an X-ray source 18 and an X-ray detector 20. The recording unit rotates about a longitudinal axis 22 during the recording of a tomographic image, and the X-ray source 18 emits X-rays 24 during a recording. While an image is being recorded a patient 26 lies on a patient bed 28. The bed 28 is connected to a table base 30 such that it supports the bed 28 bearing the patient 26. The bed 28 is designed to move the patient 26 along a recording direction through an opening or tunnel 32 of a gantry 34 of the system 12. The table base 30 includes a control unit 34 connected to a computer 36 to exchange data. In the example shown in FIG. 1, a medical diagnostic or therapeutic unit is designed in the form of a system 12 by a determination unit 38 in the form of a stored computer program that can be executed on the computer 36. The computer 36 is connected to an output unit 40 and an input unit 42. The output unit 40 is, for example, one (or more) liquid crystal display (LCD) or plasma screen(s). An output 44 on the output unit 40 comprises, for example, a graphical user interface for actuating the individual units of the system 12 and the control unit 34. Furthermore, different views of the recorded data can be displayed on the output unit 40. The input unit 42 is for example a keyboard, mouse, touch screen or a microphone for speech input.

Figure 2A:
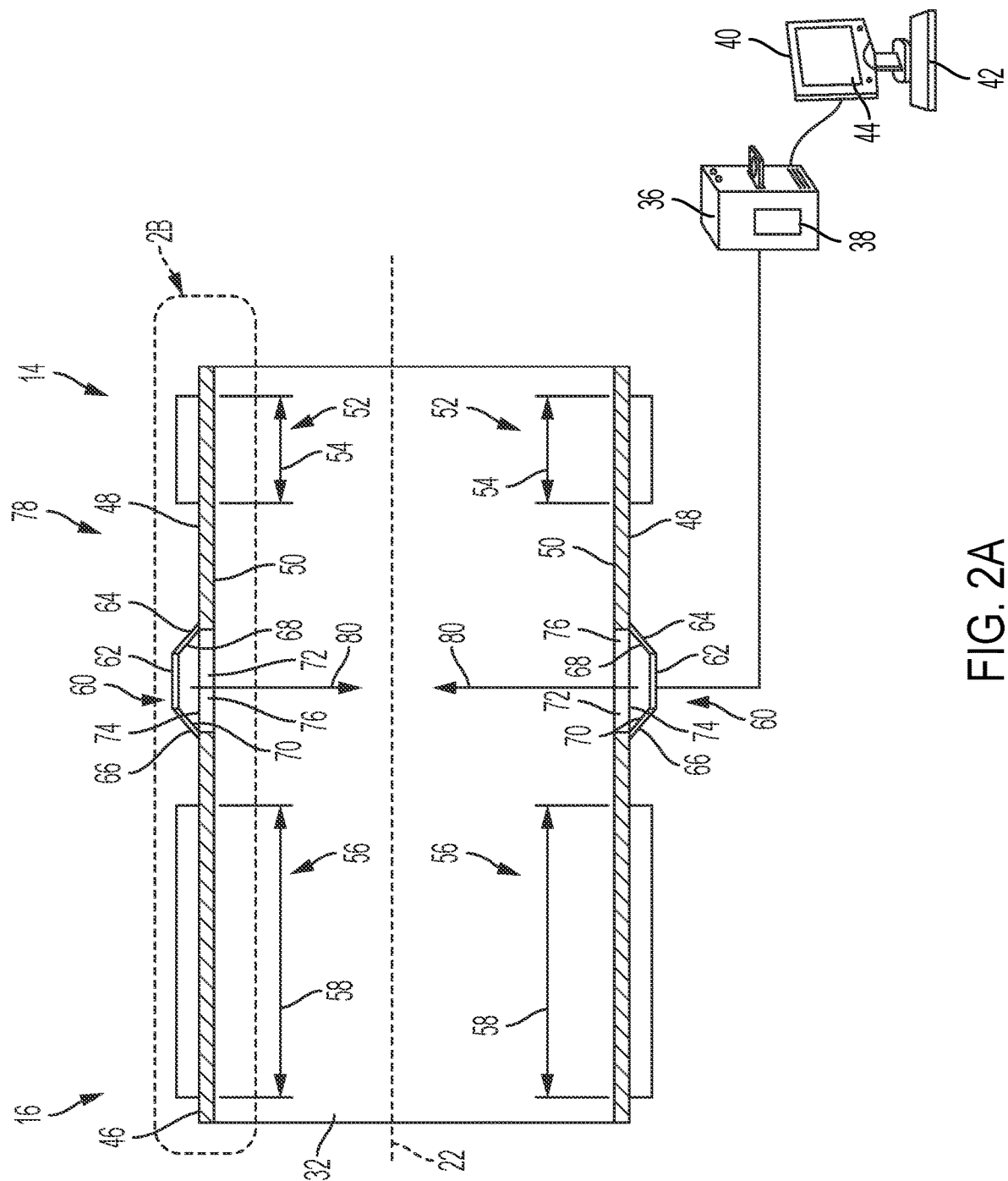
FIG. 2A depicts a lighting arrangement in accordance with an aspect of the invention.
Figure 3:
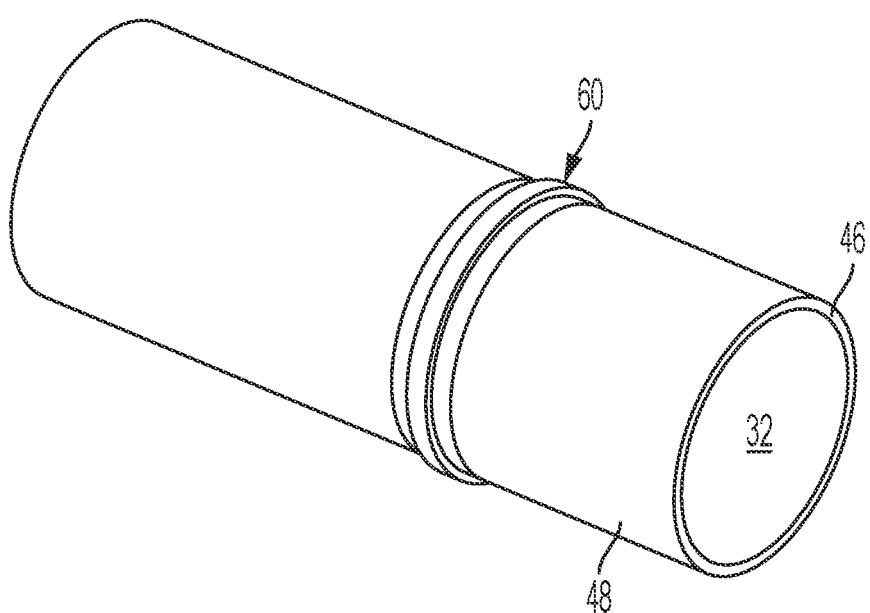
FIG. 3 is a perspective view of a wall and a lighting device.

FIG. 2A depicts a schematic cross-sectional side view of the tunnel 32. The tunnel 32 is defined by a substantially cylindrical tunnel wall 46 having outer 48 and inner 50 surfaces. The CT portion 14 includes a CT field of view 52 having a first width 54 and the PET portion 16 includes a PET field of view 56 having a second width 58. The CT 14 and PET 16 portions are sensitive to X-rays and gamma rays, respectively, via the CT 52 and PET 56 fields of view, respectively. In accordance with an aspect of the invention, a lighting device 60 is located adjacent to or on the outer surface 48 of the wall 46 and between the CT 52 and PET 56 fields of view. The lighting device 60 is also located outside of the first 54 and second 58 widths of the CT 52 and PET 56 fields of view, respectively, so that X-rays and gamma rays generated by the system 12 are not affected by the lighting device 60. FIG. 3 is a perspective view of the wall 46 and the lighting device 60. Referring to FIG. 3 in conjunction with FIG. 2A, the lighting device 60 may extend around an entire circumference of the outer surface 48 of the wall 46 to form a substantially ring-shaped configuration around the wall 46 having a central angle of 360 degrees. Alternatively, the lighting device 60 may extend only partially around the circumference of the outer surface 48 to form a semicircular (i.e. approximately 180 degrees) shape or an arc shape of either more or less than 180 approximately degrees.

Figure 2B:
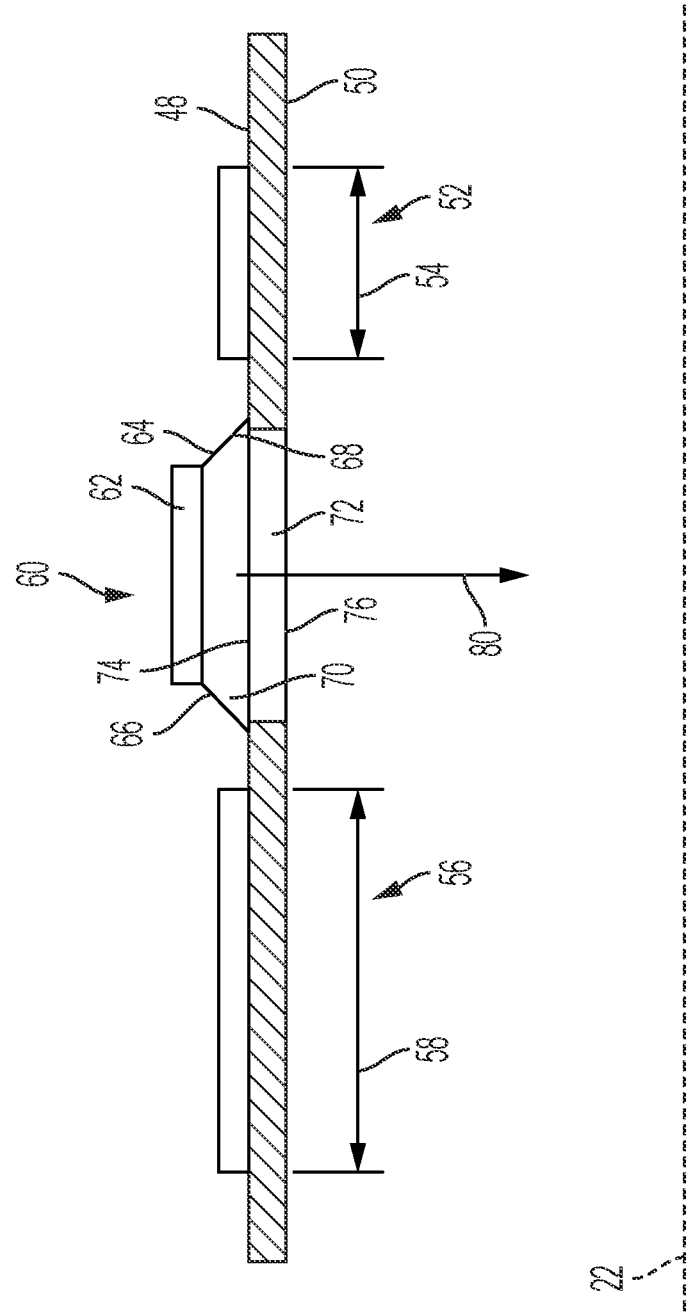
FIG. 2B is an enlarged view of region 2B of FIG. 2A.

FIG. 2B is an enlarged view of region 2B of FIG. 2A. Referring FIGS. 2A and 2B, the lighting device 60 includes a light source 62 located between first 64 and second 66 reflector elements that extend toward the outer surface 48 and contact the outer surface 48. The first 64 and second 66 reflector elements include first 68 and second 70 mirror surfaces, respectively, located to reflect light emitted by the light source 62. In an alternate embodiment, additional or fewer reflector elements and/or mirror surfaces may be used. The wall 46 includes a window or transparent wall section 72 having transparent outer 74 and inner 76 surfaces. In accordance with an aspect of the invention, the transparent inner surface 76 is aligned with the inner surface 50 of the wall 46 to form a continuously smooth inner surface. This reduces the likelihood that the patient 26 is caught or snagged when the patient 26 is moved in and out of the tunnel 32 and facilitates equipment hygiene. The transparent wall section 72 is aligned with the lighting device 60 to form a lighting arrangement 78 for illuminating the tunnel 32. In an embodiment, a light diffuser may be used instead of, or in addition to, the transparent wall section 72.

Light 80 emitted by the light source 62 travels toward the transparent wall section 72 and is reflected by the first 68 and second 70 mirror surfaces toward the transparent wall section 72. Light 80 is then transmitted through the transparent wall section 72 in a direction substantially orthogonal to the longitudinal axis 22 and into the tunnel 32 to illuminate the tunnel 32. Alternatively, light 80 may be oriented at an angle other than an orthogonal angle relative to the longitudinal axis 22. The light source 62 may be a strip of lights, a fiber optic light rope or a strip of red, green, blue (RGB) light emitting diodes (LEDs) or other light source that emits a broad light spectrum.

In an embodiment, the transparent wall section 72 corresponds to the circumferential shape of the lighting device 60. For example, the transparent wall section 72 and the lighting device 60 may both be ring-shaped such that light is transmitted through the entire circumference (i.e. 360 degrees) and into the tunnel 32 to circumferentially illuminate the tunnel 32. In an embodiment, the first 64 and second 66 reflector elements are sloped away from each other in order to provide a relatively wide-angle light beam in the tunnel 32. Alternatively, the first 64 and second 66 reflector elements may be oriented to provide other beam angles as desired, such as a relatively narrow beam angle.

Illumination of the tunnel 32 ameliorates the look and feel of the tunnel 32 and gives the tunnel 32 an appearance of being spacious to the patient 26, thus lessening the effects of claustrophobia and calming the patient 26. Further, the lighting arrangement 78 is located outside of both the CT 52 and PET 56 fields of view (i.e. outside of an imaging volume) and thus does not influence the X-rays or gamma rays generated by the system 12 and avoids attenuation and scatter of the signals.

In addition to illuminating the tunnel 32, the lighting arrangement 78 may be used to generate light that serves as a parameter indicator for a clinician or operator so that the operator is able to readily observe a status of the system 12 without having to be located at terminal or output unit 40 of the system 12. In accordance with an aspect of the invention, lighting in the tunnel 32 may be varied in intensity according to an amount of activity measured by the PET portion 16 such as a changing count rate. In addition, the lighting device 60 may provide color lighting indicative of a system status or mode to indicate that the system is on, idling, running, that the bed 28 or a patient handling system is in motion and others.

Different color lighting may be used to indicate the health of the system. For example, upon startup of the system 12, green lighting may be used to indicate a normal system operating status (i.e. ready to scan, no system issue detected and others), yellow lighting to indicate a system warning that needs attention, red lighting to indicate a system failure that needs to be resolved and blue lighting to indicate that the system 12 is in a power save mode. Further, different color lighting may be used to indicate a message or instruction to the patient. For example, a first color may be used to indicate to the patient to hold their breath, a second color to indicate to the patient that they should breathe and other colors may be used to indicate other messages. In addition, the light source 62 may be arranged in a panel configuration to form separate LEDs that each serve as pixels on a text screen. This enables the display of messages on the screen that are helpful to a patient 26 that has hearing loss or useful for studying a patient's auditory system response. For example, the messages indicating a patient instruction such as "breathe", "stop breathing", or a message indicating scan time, remaining scan time and others may be displayed on the screen. The computer 36 may be used to control activation and operation of the light source 62.

Figure 4:
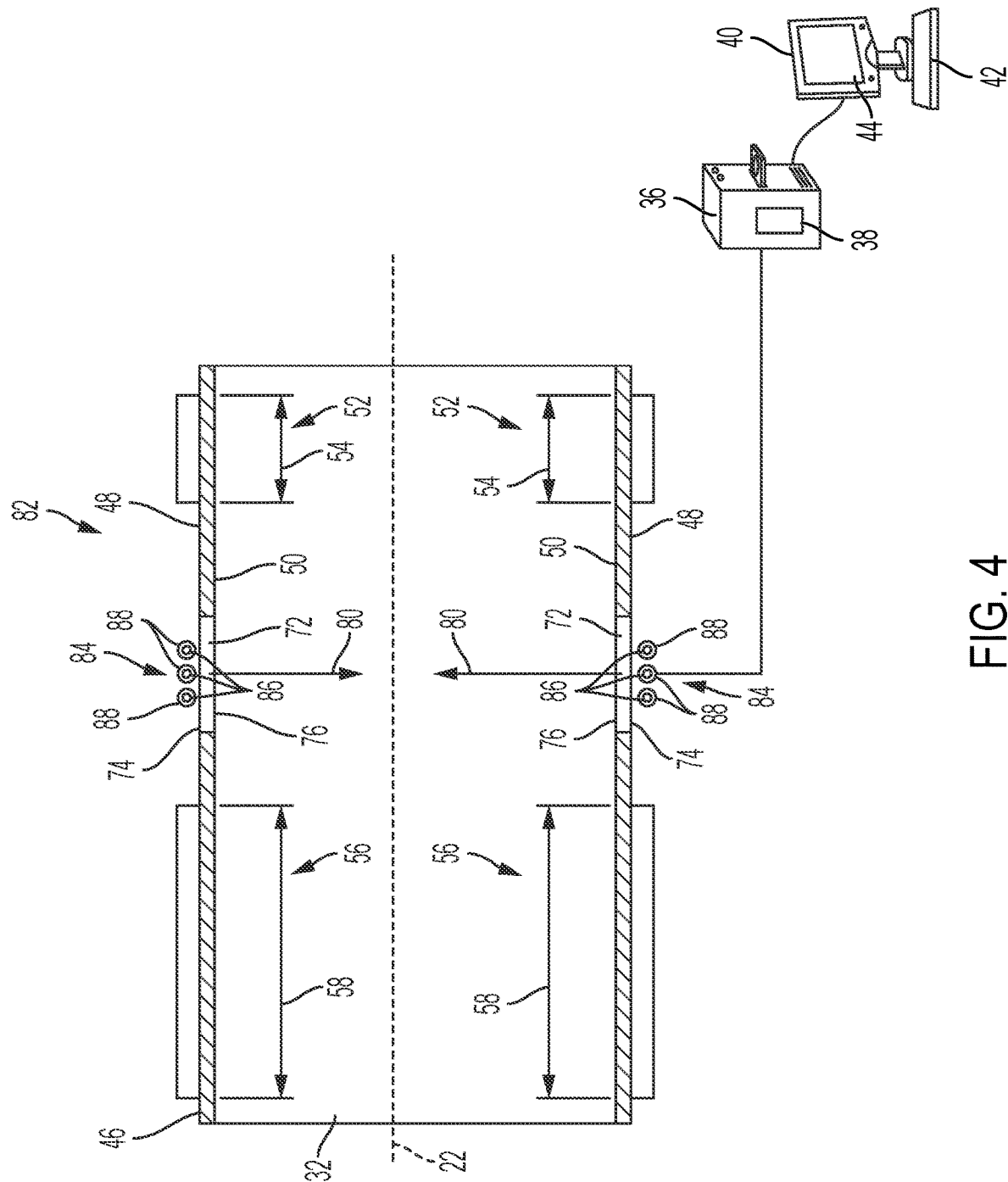
FIG. 4 depicts a lighting arrangement in accordance with an alternate embodiment of the invention.

Referring to FIG. 4, a lighting arrangement 82 for illuminating the tunnel 32 in accordance with an alternate embodiment of the invention is shown. Lighting device 84 includes at least one lighting element 86 inserted into a rope or light strip 88 of substantially transparent fiber optic material. In an embodiment, the lighting element 86 includes at least one RGB LED or other light source that emits different color light. The strip 88 is located on the transparent outer surface 74 and may extend around the entire circumference of the transparent outer surface 74 of the transparent wall section 72 to form a ring-shaped configuration having a central angle of 360 degrees around the wall 46. Alternatively, the strip 88 may extend only partially around the circumference of the transparent outer surface 74 to form a semicircular (i.e. approximately 180 degrees) shape or an arc shape of either more or less than 180 approximately degrees. More than one strip 88 may be positioned around the circumference of the transparent outer surface 74 such that the strips 88 are positioned side by side on the transparent outer surface 74 to a desired width. The strips 88 are located outside of the first 54 and second 58 widths of the CT 52 and PET 56 fields of view, respectively, so that X-rays and gamma rays generated by the system 12 are not affected by the strips 88. In an embodiment, light 80 emitted by the lighting device 84 is transmitted through the transparent wall section 72 in a direction substantially orthogonal to the longitudinal axis 22 such that light is transmitted through the entire circumference (i.e. 360 degrees) and into the tunnel 32 to circumferentially illuminate the tunnel 32. Alternatively, light 80 may be oriented at an angle other than an orthogonal angle relative to the longitudinal axis 22.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A lighting arrangement for a medical imaging system having a cylindrical wall that forms a tunnel that receives a patient to be scanned wherein the medical imaging system includes first and second imaging portions having first and second fields of view, respectively, comprising:
    a light transmitting wall section formed in the wall, wherein the light transmitting wall section extends along a light transmitting portion of a wall circumference; and
    a lighting device located adjacent an outer surface of the light transmitting wall section, wherein the lighting device extends along a device portion of a wall circumference corresponding to the light transmitting portion wherein the lighting device is located between the first and second fields of view and wherein light emitted by the lighting device is transmitted through the light transmitting wall section and into the tunnel to circumferentially illuminate the tunnel.

2. The lighting arrangement according to claim 1, wherein either the first imaging portion is a PET portion having a PET field of view and the second imaging portion is a CT portion having a CT field of view, the first imaging portion is a SPECT portion having a SPECT field of view and the second imaging portion is a CT portion having a CT field of view, the first imaging portion is an MR imaging portion having an MR field of view and the second imaging portion is a PET portion having a PET field of view or the first imaging portion is an MR portion having an MR field of view and the second imaging portion is a CT portion having a CT field of view.

3. The lighting arrangement according to claim 1, wherein the light transmitting wall section includes a light diffuser.

4. The lighting arrangement according to claim 1, wherein the lighting device includes at least one reflector element for reflecting light through the light transmitting wall section.

5. The lighting arrangement according to claim 4, wherein the reflector element includes at least one mirror surface.

6. The lighting arrangement according to claim 1, wherein a color of light emitted by the lighting device is indicative of a system status.

7. The lighting arrangement according to claim 1, wherein a color of light emitted by the lighting device indicates a message or instruction to the patient.

8. The lighting arrangement according to claim 1, wherein illumination of the tunnel by the lighting device ameliorates a look and feel of the tunnel to calm the patient.

9. The lighting arrangement according to claim 2, wherein the light emitted by the lighting device varies in intensity to indicate a changing count rate measured by the PET portion.

10. The lighting arrangement according to claim 1, wherein the light transmitting wall section and lighting device extend along the entire wall circumference.

11. A lighting arrangement for a medical imaging system having a cylindrical wall that forms a tunnel that receives a patient to be scanned wherein the medical imaging system includes first and second imaging portions having first and second fields of view, respectively, comprising:
    a light transmitting wall section formed in the wall, wherein the light transmitting wall section extends along a light transmitting portion of a wall circumference; and
    at least one light strip including at least one lighting element wherein the strip is located on an outer surface of the light transmitting wall section and extends along a strip portion of a wall circumference corresponding to the light transmitting portion wherein the light strip element is located between the first and second fields of view and wherein light emitted by the strip is transmitted through the light transmitting wall section and into the tunnel to circumferentially illuminate the tunnel.

12. The lighting arrangement according to claim 11, wherein either the first imaging portion is a PET portion having a PET field of view and the second imaging portion is a CT portion having a CT field of view, the first imaging portion is a SPECT portion having a SPECT field of view and the second imaging portion is a CT portion having a CT field of view, the first imaging portion is an MR imaging portion having an MR field of view and the second imaging portion is a PET portion having a PET field of view or the first imaging portion is an MR portion having an MR field of view and the second imaging portion is a CT portion having a CT field of view.

13. The lighting arrangement according to claim 11, wherein more than light strip is positioned on the outer surface such that the light strips are positioned side by side on the outer surface of the light transmitting wall section.

14. The lighting arrangement according to claim 11, wherein the light strip includes a light transmitting fiber optic material that includes red, green, blue (RGB) light emitting diodes (LEDs) that emit a broad light spectrum.

15. The lighting arrangement according to claim 11, wherein a color of light emitted by the light strip is indicative of a system status.

16. The lighting arrangement according to claim 11, wherein a color of light emitted by the light strip indicates a message or instruction to the patient.

17. The lighting arrangement according to claim 11, wherein illumination of the tunnel by the light strip ameliorates a look and feel of the tunnel to calm the patient.

18. The lighting arrangement according to claim 12, wherein the light emitted by the lighting device varies in intensity to indicate a changing count rate measured by the PET portion.

19. The lighting arrangement according to claim 11, wherein the light transmitting wall section and light strip extend along the entire wall circumference.

20. The lighting arrangement according to claim 11, wherein the light transmitting wall section includes a light diffuser.

21. A method of illuminating a tunnel of a medical imaging system having a cylindrical wall that forms the tunnel wherein the tunnel receives a patient to be scanned wherein the medical imaging system includes first and second imaging portions having first and second fields of view, respectively, comprising:
  providing a light transmitting wall section in the wall, wherein the light transmitting wall section extends along a light transmitting portion of a wall circumference;
  locating a lighting device adjacent an outer surface of the light transmitting wall section and between the first and second fields of view, wherein the lighting device extends along a device portion of a wall circumference corresponding to the light transmitting portion;
  transmitting light emitted by the lighting device through the light transmitting wall section and into the tunnel;
  circumferentially illuminating the tunnel and;
  transmitting a color of light that is indicative of a system status.

* * * * *